United States Patent [19]

Hamaguchi et al.

[11] Patent Number: 4,863,859
[45] Date of Patent: Sep. 5, 1989

[54] PROCESS FOR PREPARING OPTICALLY ACTIVE GLYCEROL DERIVATIVES

[75] Inventors: Shigeki Hamaguchi; Takehisa Ohashi, both of Kobe; Kiyoshi Watanabe, Akashi, all of Japan

[73] Assignee: Kanegafuchi Kagaku Kogyo Kabushiki Kaisha, Osaka, Japan

[21] Appl. No.: 822,494

[22] Filed: Jan. 27, 1986

[30] Foreign Application Priority Data

Jan. 28, 1985 [JP] Japan .................................. 60-13881
Mar. 15, 1985 [JP] Japan .................................. 60-53188

[51] Int. Cl.$^4$ ........................ C12P 11/00; C12P 41/00
[52] U.S. Cl. .................................. 435/130; 435/280
[58] Field of Search ............... 435/130, 159, 874, 917, 435/931, 939, 280, 135, 198, 197

[56] References Cited

U.S. PATENT DOCUMENTS 4,408,063 10/1983 Baldwin et al. ...................... 549/518
4,745,066 5/1988 Hamaguchi et al. ............... 435/280

OTHER PUBLICATIONS

Hamaguchi et al, Lipase-Catalyzed Stereoselective Hydrolysis of 2-Acyloxy-3-Chlorpropyl P-Toluenesulfonate, Agric. Biol. Chem. 50(2), 375-380, 1986.
Iriuchijima et al, Asymmetric Hydrolysis of (±)1,2-Diacetoxy-3-Chloropropane and Its Related Compounds with Lipase, Synthesis of Optically Pure (S)-Propranolol, Agric. Biol. Chem., 46(5), 1153-1157, 1982.
European Search Report for EP 86 10 1018 and Annex thereto.
Agric. Biol. Chem., vol. 46 (5), 1153 to 1157; (6), 1593 to 1597 (1982).

*Primary Examiner*—Charles F. Warren
*Assistant Examiner*—Gail Knox

[57] ABSTRACT

A process for preparing optically active glycerol derivatives by a biochemical resolution which comprises (i) subjecting an ester having the general formula [(R,S)-I]:

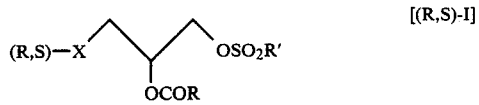

wherein X is a halogen atom, R is an aliphatic hydrocarbon group of $C_1$ to $C_8$ and R' is an aromatic hydrocarbon group or an aliphatic hydrocarbon group of $C_1$ to $C_2$, to the action of enzymes derived from either microorganisms or animal organs, wherein said enzymes have a stereo selective esterase activity to asymmetrically hydrolyze the ester having the general formula [(R,S)-I] to give a mixture of an optically active alcohol having the general formula (II)*:

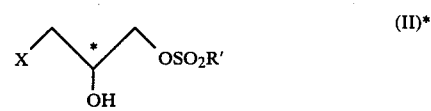

wherein X and R' are as above and an optically active ester having the general formula (I)*:

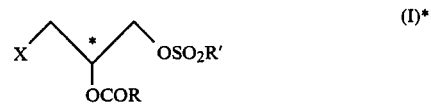

wherein X, R and R' are as above, and (ii) obtaining the optically active alcohol having the general formula (II)* and the optically active ester having the general formula (I)* by separating operations.

In accordance with the present invention, there can be provided a process for preparing optically active glycerol derivatives, wherein the optically active ester having the general formula (I)* and the optically active alcohol having the general formula (II)* can be easily obtained.

2 Claims, No Drawings

PROCESS FOR PREPARING OPTICALLY ACTIVE GLYCEROL DERIVATIVES

BACKGROUND OF THE INVENTION

The present invention relates to a process for preparing optically active glycerol derivatives by a biochemical resolution which comprises (i) subjecting an ester having the general formula [(R,S)-I]:

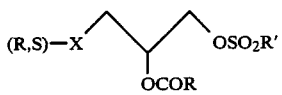

[(R,S)-I]

wherein X is a halogen atom, R is an aliphatic hydrocarbon group of $C_1$ to $C_8$ and R' is an aromatic hydrocarbon group or an aliphatic hydrocarbon group of $C_1$ to $C_2$, to the action of enzymes derived from either microorganisms or animal organs, wherein said enzymes have a stereo selective esterase activity to asymmetrically hydrolyze the ester having the general formula [(R,S)-I] to give a mixture of an optically active alcohol having the general formula (II)*:

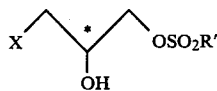

(II)* wherein X and R' are as above and an optically active ester having the general formula (I)*:

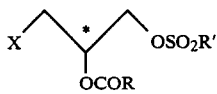

(I)* wherein X, R and R' are as above and (ii) obtaining the optically active alcohol having the general formula (II)* and the optically active ester having the general formula (I)* by separating operations.

The above optically active glycerol derivatives, both (R)-form and (S)-form, are very useful compounds that can be converted to various kinds of optically active drugs such as, for instance, l-carnitine, (S)-β-blocker and optically active platelet activating factor antagonists.

It has been known that these optically active glycerol derivatives could be synthesized from D-mannitol (J. J. Baldwin et al., J. Org. Chem., 43, 4876 (1978)). However, this process is not suitable for an industrial scale production of the optically active glycerol derivatives since the process requires many manufacturing steps and an employment of heavy metal such as lead tetraacetate. Consequently, it has been earnestly desired to establish a simple process for preparing the optically active glycerol derivatives.

The present inventors have been studied on an asymmetrical hydrolysis of the racemic ester having the general formula [(R,S)-I] by subjecting the ester having the general formula [(R,S)-I] to the action of the enzymes having a stereo selective esterase activity in order to obtain an optically active alcohol and ester, and it was found that enzymes prepared from microorganisms of such genus as Pseudomonas, Chromobacterium, Aspergillus, Mucor or Rhizopus or enzymes prepared from animal organs could asymmetrically hydrolyze the ester having the general formula [(R,S)-I] to give the unchanged ester having the general formula

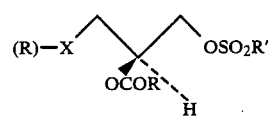

[(R)-I]

wherein X, R and R' are as above, and the alcohol having the general formula [(S)-II]:

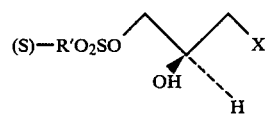

[(S)-II]

wherein X and R' are as above.

The optically active ester having the general formula (I)* can be easily converted into the corresponding alcohol having the general formula (II)* by chemical hydrolysis.

The ester (I)* and alcohol (II)* can be easily obtained by separating operation such as silica-gel column-chromatography and each ester and alcohol is obtained.

SUMMARY OF THE INVENTION

In accordance with the present invention, there can be provided a process for preparing optically active glycerol derivatives, wherein the optically active ester having the general formula (I)* and the optically active alcohol having the general formula (II)* can be easily obtained.

DETAILED DESCRIPTION OF THE INVENTION

The substitutents X, R and R' in the general formula [(R,S)-I] of the ester employed for a substrate in the present invention are explained in more detail.

The substitutent X is a halogen atom such as, for instance, chlorine or bromine. The substituent R is an aliphatic hydrocarbon group of $C_1$ to $C_8$, preferably an aliphatic hydrocarbon group of $C_1$ to $C_3$ in view point of a hydrolysis rate. The aliphatic hydrocarbon group may be substituted with a halogen group or hydroxyl group The substituent R' is an aromatic hydrocarbon group such as, for instance, tolyl, phenyl or naphthylene, or an aliphatic hydrocarbon group such as, for instance, methane or ethane. The aromatic hydrocarbon group or the aliphatic hydrocarbon group may be substituted with a halogen atom or hydroxyl group.

In order to obtain the starting ester [(R,S)-I], an equimolar amount of sulfonic acid and epichlorohydrin are reacted in the presence of conventional organic solvent such as dichrolomethane or ethyl acetate, or without solvent while cooling, to give the racemic alcohol having the general fomula [(R,S)-II]:

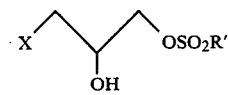

[(R,S)-II]

wherein X and R' are as above, quantitatively, and then hydroxyl group at 2-postion of the alcohol is converted into ester by reacting the alcohol [(R,S)-II] with acid chloride or acid anhydride in the presence of basic compound such as, for instance, pyridine or triethylamine in an innert solvent such as dichrolomethane or ethyl acetate while cooling to give the racemic ester [(R,S)-I], which is then washed with water and concentrated. By such procedure, the starting ester [(R,S)-I] is prepared.

Any enzyme may be employed, which has a stereo selective esterase activity to asymmetrically hydrolyze the racemic ester [(R,S)-I] to produce the ester [(R)-I] and the alcohol [(S)-II]. Enzymes employed in the present invention are prepared from microorganism for example, such genus as *Pseudomonas, Chromobacterium, Aspergillus, Mucor* or *Rhizopus*, more specifically those derived from such microorganism as *Aspergillus niger, Rhizopus delemar* or *Rhizopus japonicus*. Also enzymes prepared from animal organs such as pancreas or liver of cattle or pig can be used. The enzymes are commercially available as lipoprotein lipase Lipase AP6, Lipase M-AP-10, Lipase D, Lipase F-AP 15, Pancreatic digesting enzyme TA (Amano Pharmaceutical Co., Ltd.), lipase (Toyo jyozo Co., Ltd., Carbio chem. Co., Ltd.), Saiken 100 (Nagase & Company, Ltd.) and Steapsin (Wako Purechemical Industries, Ltd.)

The asymmetric hydrolysis is carried out in such a way that 2 to 80% (w/v) of the substrate of the racemic ester [(R,S)-I] is suspended in the reaction solution, to which the enzyme is added in a suitable amount, for instance, in a ratio of 1:1 to 1:1000 (enzyme: substrate), and the reaction is proceeded at 10° to 40° C., preferably 25° to 35° C. An amount of the remaining substrate and an amount of the reaction product are measured by high performance liquid chromatography (HPLC) and the reaction is stopped when 1:1 of a molar ratio of the ester (I)* and the alcohol (II)* in the reaction solution is obtained.

The reaction may be conducted at the pH value ranging from 4 to 8.5. A neutralizing agent such as NaOH solution is preferably employed to maintain the pH value in the range of 6 to 7.5 since the pH value of the reaction solution is inclined to shift to the acidic side as the reaction proceeds.

Further, immobilization of the enzyme makes it possible to conduct the above asymmetric hydrolysis repeatedly.

After completion of the reaction, the ester (I)* and the alcohol (II)* are easily separated in such a way that both ester and alcohol are extracted with an organic solvent such as, for instance, dichrolomethane or ethyl acetate, and the extract is then concentrated and subjected to silica-gel column-chromatography.

The optically active ester (I)* obtained after separation may be concentrated, as it is, to give the ester with a high optical purity, or may be hydrolyzed under acidic condition to give the corresponding alcohol (II)*. For a sythesis of l-carnitine, the obtained ester (I)* is reacted with sodium cyanide in a methanol solution and the acyl group of the ester (I)* at 2-position being removed simultaneously to produce γ-halogeno-β-hydroxy butyronitril.

The present invention is more specifically described and explained by the following Reference Examples and Examples. It is to be understood that the present invention is not limited to Reference Examples and Examples, and various changes and modifications may be made without departing from the spirit and scope of the present invention.

REFERENCE EXAMPLE 1 [Preparation of (R,S)-3-chloro-2-acetoxypropyl p-toluenesulfonate having the formula [(R,S)-Ia₁]]

[(R,S)-Ia₁]

Fifty grams of epichlorohydrine was slowly added dropwise to a suspension of 95.9 of p-toluenesulfonic acid.H₂O(TsOH.H₂O) and 500 ml of dichrolomethane and the mixture was reacted at room temperature for 6 hours. The reaction mixture was concentrated under reduced pressure to give 128 g of (R,S)-3-chloro-2-hydroxypropyl p-toluenesulfonate having the formula [(R,S)-IIa]:

[(R,S)-IIa]

Nuclear magnetic resonance spectrum ($^1$H NMR) (90 MHz) and elementary analysis of the obtained compound were as follows: $^1$H NMR (CDCl₃)δ(ppm): 2.44 (3H, s, CH₃-Ar), 2.98 (1H, broad, OH), 3.50 to 4.32 (5H, m, —CH₂CH(OH)CH₂—), 7.30 and 7.75 (4H, 2d, J=8.7Hz, Ar-H)

Elementary analysis for C₁₀H₁₃ClO₄S Calcd.(%): C 45.37, H 4.95; Found (%): C 45.39, H 4.89.

Into 500 ml of dichloromethane were dissolved 28 g of the obtained compound [(R,S)-IIa] and 60 g of triethyl amine, to which 44 g of acetylchloride was added dropwise for 30 minutes while cooling with ice bath and the mixture was reacted at room temperature for 3 hours.

The reaction progress was measured by monitoring with high performance liquid chromatography (hereinafter referred to as "HPLC") analysis. After completion of the reaction, the reaction mixture was washed twice with an equal amount of water, which was then concentrated under reduced pressure to give a syrup of (R,S)-3-chloro-2-acetoxypropyl p-toluenesulfonate [(R,S)-Ia₁] (yield: 131 g).

Further, a part of the obtained product was recrystallized in ethyl acetate-hexane (1:1) to give colorless crystals (melting point: 41.5° to 42.0° C).

$^1$H NMR (90 MHz) and elementary analysis of the crystals were as follows:

$^1$H NMR (CDCl₃) δ(ppm): 2.01 (3H, s, CH₃CO—), 2.45 (3H, s, CH₃—Ar), 3.61 (2H, d, J=6.0Hz, —CH₂—), 4.20 (2H, d, J=5.4Hz, —CH₂—), 4.93 to 5.26 (1H, m, —CH—), 7.33 and 7 75 (4H, 2d, J=9.0Hz, Ar-H)

Elementary analysis for C₁₂H₁₅ClO₅S: Calcd.(%): C 46.98, H 4.93; Found (%): C 46.78, H 4.81.

As a substrate of the hydrolysis, the syrup of the compound [(R,S)-Ia₁] (purity: 95%) was employed.

REFERENCE EXAMPLE 2

[Preparation of (R,S)-3-chloro-2-butanoyloxypropyl p-toluenesulfonate having the formula [(R,S)-Ia₂2]]

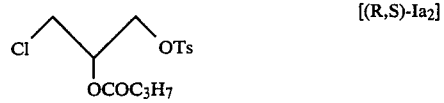

The procedure of Reference Example 1 was repeated except that butanoyl chloride was employed in place of acetyl chloride to give a syrup of the compound (R,S)-Ia₂ 2].

¹H NMR and elementary analysis of the obtained compound were as follows:

¹H NMR (90 MHz, CDCl₃) δ(ppm): 0.93 (3H, t, J=6.3Hz, CH₃CH₂CH₂—), 1.45 to 1.78 (2H, m, CH₃CH₂CH₂—) 2.26 (2H, t, J=7.3Hz, CH₃CH₂CH₂—), 2.43 (3H, s, CH₃—Ar), 3.58 (2H, d, J=5.7Hz, —CH₂—), 4.17 (2H, d, J=3.9Hz, —CH₂—), 4.92 to 5.20 (1H, m, —CH—), 7.31 and 7.74 (4H, 2d, J=8.7Hz, Ar-H) Elementary analysis for C₁₄H₁₉ClO₅S: Calcd.(%): C 50.22, H 5.72; Found (%): C 50.31, H 5.88.

REFERENCE EXAMPLE 3 [Preparation of (R,S)-3-chloro-2-butanoyloxypropyl methanesulfonate having the formula [(R,S)-Ib]]

Into a solution of 48 g of methanesulfonic acid in 200 ml of dichlorolomethane was added dropwise 50 g of epichlorohydrine for 30 minutes and the reaction was carried out at 40° C. for 3 hours. The reaction mixture was concentrated under reduced pressure to give 92 g of (R,S)-3-chrolo-2-hydroxypropyl methanesulfonate [(R,S)-IIb]:

¹H NMR (90 MHz) and elementary analysis of the obtained compound were as follows:

¹H NMR (CDCl3) δ(ppm): 3.11 (3H, s, CH₃SO₂), 3.90 to 4.38 (5H, m, —CH₂CH(0—)CH₂—) and 5.96 (1H, s, OH) Elementary analysis for C₄H₉ClO₄S: Calcd.(%): C 25.47, H 4.81; Found (%): C 25.60, H 4.89.

Fifty five grams of triethylamine was added dropwise to a mixture of 92 g of the compound [(R,S)-IIb], 500 ml of dichlorolomethane and 56 g of butanoyl chloride for 30 minutes while cooling with ice bath and the reaction was carried out at room temperature for 3 hours.

The reaction progress was measured by monitoring with a thin layer chromatography (hereinafter referred to as "TLC") (Merck silicagel 60 F₂₅₄ plate, developer: dichlorolomethane, detection: color development with phosphorus-molybdic acid). After completion of the reaction, the reaction mixture was washed twice with an equal amount of water, which was then concentrated under reduced pressure to give a syrup of (R,S)-3-chloro-2butanoyloxypropyl methanesulfonate [(R,S)-Ib] (yield: 52.6 g).

¹H NMR (90 MHz) and elementary analysis of the obtained compound were as follows: ¹H NMR(CDCl₃) δ(ppm): 0.97 (3H, t, J=7.6 Hz, CH₃CH₂—), 1.48 to 1.80 (2H, m, CH₃CH₂CH₂—), 2.35 (3H, t, J=7.2Hz, CH₃CH₂CH₂—, 3.07 (3H, s, CH₃S02—), 3.45 to 3.86 (4H, m, CH₂CH(O —)CH₂—) and 5.03 to 5.27 (1H, m, —CH₂CH(O —)CH₂) Elementary analysis for C₈H₁₅ClO₅S: Calcd.(%): C 37.14, H 5.84; Found (%): C 37.25, H 5.98.

EXAMPLE 1

There were added 20 g of the substrate [(R,S)-Ia₁] and 0.2 g of Lipoprotein lipase Amano 3 to 100 ml of a 0.1M phosphate buffer (pH 7.0) and the asymmetric hydrolysis was carried out with stirring at 30° C. for 24 hours while pH was maintained to 7.0 with 2.5N NaOH solution. [R,Ia₁] and [S-IIa] were extracted twice with 200 ml of dichrolomethane and the dichrolomethane layer was dehydrated with anhydrous sodium sulfate and was concentrated under reduced pressure. The resultant concentrate was subjected to a silica-gel column-chromatography (Wakogel C-200, L/D=50/2.6 cm), developer: hexane-acetone=6:1 to 4:1 (v/v)) and each fraction of [(R)-Ia₁] and [(S)-IIa] was collected and concentrated under reduced pressure to give 8.5 g of [(R)-Ia₁] and 7.4 g of [(S)-IIa].

Specific rotatory power of each compound was measured as follows:

The compound [(R)-Ia₁]
 $[\alpha]_D^{20} -9.2°$ (c=5.0, MeOH)
The compound [(S)-IIa]:
 $[\alpha]_D^{20} -2.2°$ (c=5.0, MeOH)

[(R)-IIa] was obtained by treatment of the compound [(R)-Ia₁] with 100 ml of 1N hydrochloric acid solution ($[\alpha]_D^{20}+2.1°$ (c=5.0, MeOH)). On the other hand, [(S)-IIa] was acetylated to give [(S)-Ia₁] and a specific rotatory power was $[\alpha]_D^{20}+9.4°$ (c=5.0, MeOH).

By the HPLC analysis of [(R)-Ia₁] and [(S)-IIa], it was confirmed that both compounds had a high optical purity (not less than 99% e.e.).

HPLC analysis was conducted as follows:
HPLC column: Chiral CEL OC (made by Japan Spectroscopic Co., Ltd.)
Developer: hexane-isopropanol=9:1
Flow rate: 2 ml/minute
Amount of a sample: 1 μl (1% (w/v))
Retention time
 The compound [(S)-Ia₁]: 16.0 minutes
 The compound [(R)-Ia₁]: 17.5 minutes
 The compound [(S)-IIa]: 15.0 minutes
 The compound [(R)-IIa]: 16.6 minutes

EXAMPLE 2

The procedure of Example 1 was repeated except that a compound [(R,S)-Ia₂] was employed as a substrate to give 9.0 g of [(R)-Ia₂] and 6.7 g of [(S)-IIa].

Specific rotatory power: and optical purity of the compounds were as follows:
The compound [(R)-Ia₂]
 Specific rotatory power: $[\alpha]_D^{20} -9.1°$ (c=5.0, MeOH)
 Optical purity: >99% e.e.
The compound [(S)-IIa]
 Specific rotatory power: $[\alpha]_D^{20} -1.95$ (c=5.0, MeOH)
 Optical purity: >99% e.e.

The optical purity was measured as in Example 1.
Retention time
  The compound [(S)-Ia$_2$]: 9.6 minutes
  The compound [(R)-Ia$_2$]: 10.5 minutes

EXAMPLE 3

There were added 2.0 g of the substrate [(R,S)-Ia$_1$] and 0.02 g of a Lipase (Carbiochem) to 10 ml of a 0.1M phosphate buffer (pH 7.0) and the asymmetric hydrolysis was carried out with stirring at 30° C. for 24 hours while pH being maintained to pH 7.0 with 1N NaOH solution The extraction and the separation were carried out as in Example 1 to give 0.65 g of the compound [(R)-Ia1] and 0.74 g of the compound [(S)-IIa].

Specific rotatory power and optical purity of each compound were as follows
The compound [(R)-Ia$_1$]:
  $[\alpha]_D^{20}$ −9 2° (c=5.0,MeOH)
  Optical purity:>99% e.e. The compound [(S)-IIa].
  $[\alpha]_D^{20}$ −2.15° (c=5.0,MeOH)
  Optical purity: >99% e.e.

EXAMPLE 4

There were added 2.0 g of the substrate [(R,S)-Ib] and 0.02 g of Lipoprotein lipase to 10 ml of a 0.1M phosphate buffer (pH 7.0) and the asymmetric hydrolysis was carried out with stirring at 30° C. for 24 hours while pH being maintained 7.0 with 1N NaOH solution. The extraction and the separation were carried out as in Example 1 to give 0.42 g of the compound [(R)-Ib] and 0.24 g of the compound [(S)-IIb]. The compound [(R)-Ib]: $[\alpha]_D^{20}$ −5.2° (c=2.0,MeOH)
The compound [(S)-IIb]:
  $[\alpha]_D^{20}$ −4.6° (c=2.0,MeOH)
The literature [(J. J. Baldwin et al., J. Org. Chem. 43, 4876 (1978)) [(R)-IIb]: $[\alpha]_D^{20}$+7° (c=5.78,MeOH)]

EXAMPLE 5

There were added 2.0 g of the substrate [(R,S)-Ia$_1$] and 0.2 g of Lipase D (prepared from *Rhizopus delemar*) to 20 ml of a 0.1M phosphate buffer (pH 7.0) and the asymmetric hydrolysis was carried out with stirring at 30° C. for 48 hours while pH being maintained to 7.0 with 1.0N NaOH solution. [(R)-Ia$_1$] and [(S)-IIa] were extracted twice with 40 ml of dichrolomethane and the dichrolomethane layer was dehydrated with anhydrous sodium sulfate and was concentrated under reduced presure. The resultant concentrate was subjected to a silica-gel column-chromatography (Wakogel C-200, L/D=30/1.9 cm, developer: hexane-acetone=6:1 to 4:1 (v/v)). Each fraction of [(R)-Ia$_1$] and [(S)-IIa] was collected and concentrated under reduced pressure. [(R)-Ia$_1$] was further recrystallized and 0.58 g of [(R)-Ia$_1$] and 0.72 g of [(S)-IIa] were obtained.
The compound [(R)-Ia$_1$]: $[\alpha]_D^{20}$ −8.6° (c=5.0,MeOH)
The compound [(S)-IIa]:
  $[\alpha]_D^{20}$ −1.9° (c=5.0,MeOH)

[(R)-IIa] was obtained by treatment of [(R)-Ia$_1$] with 100 ml of 1N hydrochloric acid solution ($[\alpha]_D^{20}$+1.7° (c=5.0,MeOH)). On the other hand, [(S)-IIa] was acetylated and further recrystallized to give [(S)-Ia$_l$] ($[\alpha]_D^{20}$+8.8° (c=5.0,MeOH))

By the HPLC analysis, it was confirmed that each compound had a high optical purity (not less than 99 e.e.)

HPLC analysis was conducted as in Example 1.

EXAMPLE 6

The procedure of Example 5 was repeated except that the compound [(R,S)-Ia$_2$] was employed as a substrate to give 0.84 g of the compound [(R)-Ia$_2$] and 0.69 g of the compound [(S)-IIa].
The compound [(R)-Ia$_2$]:
  $[\alpha]_D^{20}$ −8.3° (c=5.0,MeOH)
  Optical purity: >90% e.e.
The compound [(S)-IIa]: $[\alpha]_D^{20}$ −1.7° (c=5.0,MeOH)
  Optical purity: >90% e.e.

The optical purity was measured as in Example 1.
Retention time is as follows:
  The compound [(S)-Ia]$_2$]: 9.6 minutes
  The compound [(R)-Ia$_2$]: 10.5 minutes

EXAMPLES 7 to 12

There were added 1.0 g of the substrate (R,S)-Ia$_1$] and 0.2 g of each commercially available enzyme shown in Table 1 to 10 ml of a 0.1M phosphate buffer (pH 7.0) and the asymmetric hydrolysis reaction was carried out with stirring at 30° C. for 48 hours while pH being maintained to 7.0 with 1N NaOH solution. The extraction and the separation were carried out as in Example 1 to give the compound [(R)-Ia$_1$] and the compound (S)-IIa].

The results are shown in Table 1.

TABLE 1

| | | | | Compound having the formula [(R)-Ia$_1$] | | |
|---|---|---|---|---|---|---|
| Ex. No. | Enzyme | Origin | Name of Company | Yield (g) | $[\alpha]_D^{20}$ (c = 5.0, MeOH) | Optical purity (% e.e.) |
| 7 | Lipase Ap-6 | *Aspergillus niger* | Amano Pharmaceutical Co., Ltd. | 0.32 | −8.1° | 85 |
| 8 | Lipase M-AP-10 | Mucor | " | 0.25 | −8.3° | 90 |
| 9 | Lipase F-AP-15 | *Rhizopus japonicus* | " | 0.28 | −8.2° | 84 |
| 10 | Saiken 100 | *Rhizopus japonicus* | Nagase & Company, Ltd. | 0.31 | −5.6° | 63 |
| 11 | Pancreatic digesting enzyme TA | Pancreas of pig | Amano Parmaceutical Co. Ltd. | 0.30 | −4.9° | 55 |
| 12 | Steapsin | Pancreas of pig | Wako Purechemical Industries, Ltd. | 0.27 | −5.7° | 62 |

| | Compound having the formula [(R)-IIa] | |
|---|---|---|
| | Yield | $[\alpha]_D^{20}$ (c = 5.0, | Optical purity |

TABLE 1-continued

| Ex. No. | (g) | MeOH) | (% e.e.) |
|---|---|---|---|
| 7 | 0.24 | −1.7° | 88 |
| 8 | 0.25 | −1.6° | 85 |
| 9 | 0.21 | −1.6° | 82 |
| 10 | 0.32 | −0.9° | 40 |
| 11 | 0.29 | −0.8° | 48 |
| 12 | 0.28 | −1.0° | 53 |

EXAMPLE 13

There were added 2.0 g of the substrate having the formula [(R,S)-Ib] and 0.20 g of Lipase D to 10 ml of a 0.1M phosphate buffer (pH 7.0) and the asymmetric hydrolysis was carried out with stirring at 30° C. for 48 hours. The extraction and the separation were carried out as in Example 1 to give 0.35 g of the compound [(R)-Ib] and 0.40 g of the compound [(S)-IIb].

The compound [(R)-Ib]: $[\alpha]_D^{20} -4.4°$ (c=2.0,MeOH)
The compound [(S)-IIb]: $[\alpha]_D^{20} -3.9$
The literature [(J. J. Baldwin et al., J. Org. Chem. 43, 4876 (1978)
The compound having the formula [(R)-IIb]: $[\alpha]_D^{22} +7.1°$ (c=5.78,MeOH)]

What we claim is:

1. A process for preparing optically active glycerol derivatives by a biochemical resolution which comprises (i) subjecting an ester having the general formula [(R,S)-I]:

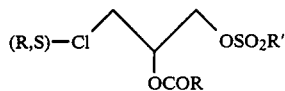
[(R,S)-I]

where in R is a methyl to the action of an having stereoselective esterase activity to give a mixture of (S)-alcohol having the general formula: [(s)-II]:

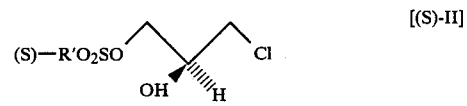
[(S)-II]

wherein R' is as above, and (R)-ester having the general formula: [(R)-I]:

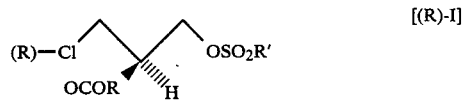
[(R)-I]

wherein R and R' are as above, and (ii) separating the (s)-alcohol having the general formula and the [(S)-II] (R)-ester having the general formula. [(R)-I].

2. The process of claim 1, wherein the enzyme is a member selected from the group consisting of lipoprotein lipase Amano 3, Lipase (Carbiochem), Lipase D, Lipase AP-6, Lipase M-AP-10, Lipase F-AP-15, Saiken 100, pancreatic digesting enzyme TA and Steapsin.

* * * * *